US011241564B2

United States Patent
Casiello et al.

(10) Patent No.: US 11,241,564 B2
(45) Date of Patent: *Feb. 8, 2022

(54) HIGH-FLOW PORT AND INFUSION NEEDLE SYSTEMS

(71) Applicant: AngioDynamics, Inc., Latham, NY (US)

(72) Inventors: Damon Casiello, Lowell, MA (US); Mark Girard, Medway, MA (US)

(73) Assignee: AngioDynamics, Inc., Latham, NY (US)

( * ) Notice: Subject to any disclaimer, the term of this patent is extended or adjusted under 35 U.S.C. 154(b) by 634 days.

This patent is subject to a terminal disclaimer.

(21) Appl. No.: 16/179,498

(22) Filed: Nov. 2, 2018

(65) Prior Publication Data

US 2019/0070399 A1    Mar. 7, 2019

Related U.S. Application Data

(63) Continuation-in-part of application No. 14/593,502, filed on Jan. 9, 2015, now Pat. No. 10,166,321.

(Continued)

(51) Int. Cl.
| | |
|---|---|
| *A61M 39/04* | (2006.01) |
| *A61L 31/06* | (2006.01) |
| *A61M 1/36* | (2006.01) |
| *A61M 39/02* | (2006.01) |
| *A61M 5/32* | (2006.01) |
| *A61M 5/158* | (2006.01) |
| *A61L 29/12* | (2006.01) |
| *A61M 39/00* | (2006.01) |
| *A61M 1/34* | (2006.01) |

(52) U.S. Cl.
CPC ........... *A61M 39/04* (2013.01); *A61L 29/126* (2013.01); *A61L 31/06* (2013.01); *A61M 1/3653* (2013.01); *A61M 1/3659* (2014.02); *A61M 1/3661* (2014.02); *A61M 5/158* (2013.01); *A61M 5/3286* (2013.01); *A61M 39/0208* (2013.01); *A61M 39/0247* (2013.01); *A61M 1/3496* (2013.01); *A61M 2039/0036* (2013.01); *A61M 2039/0205* (2013.01); *A61M 2039/0258* (2013.01); *A61M 2039/0273* (2013.01); *A61M 2039/0276* (2013.01); *A61M 2205/0216* (2013.01); *A61M 2205/04* (2013.01)

(58) Field of Classification Search
CPC .... A61L 29/126; A61L 31/06; A61M 1/3496; A61M 1/3653; A61M 1/3659; A61M 1/3661; A61M 2039/0036; A61M 2039/0205; A61M 2039/0258; A61M 2039/0273; A61M 2039/0276; A61M 2205/0216; A61M 2205/04; A61M 39/0208; A61M 39/0247; A61M 39/04; A61M 5/158; A61M 5/3286
See application file for complete search history.

(56) References Cited

U.S. PATENT DOCUMENTS 6,039,712 A  *  3/2000 Fogarty ............. A61M 39/0208
                                                                    604/175
10,166,321 B2 *  1/2019 Casiello ............... A61M 5/3286

* cited by examiner

*Primary Examiner* — Brandy S Lee
(74) *Attorney, Agent, or Firm* — Peter J. Flora, Esq.

(57) ABSTRACT

The present invention relates to a multi-reservoir port, catheter, and non-coring needle system that supports high-flow applications such as hemodialysis and apheresis. In particular, the invention relates to improvements to provide optimal flow rates, septum life, and septum/needle stability when introducing fluid into the multi-reservoir port.

18 Claims, 9 Drawing Sheets

Related U.S. Application Data

(60) Provisional application No. 61/925,287, filed on Jan. 9, 2014.

NEEDLE GAUGE (SINGLE PROFILE)

(OVERLAPPING PROFILE)

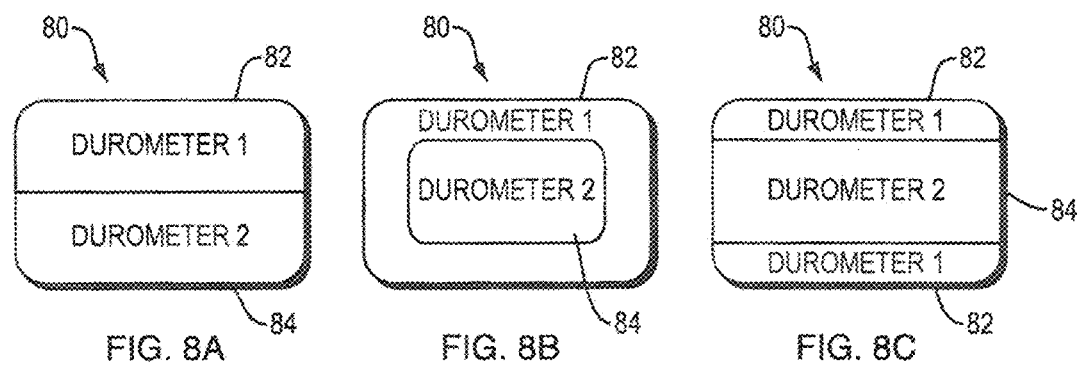
FIG. 8A  FIG. 8B  FIG. 8C
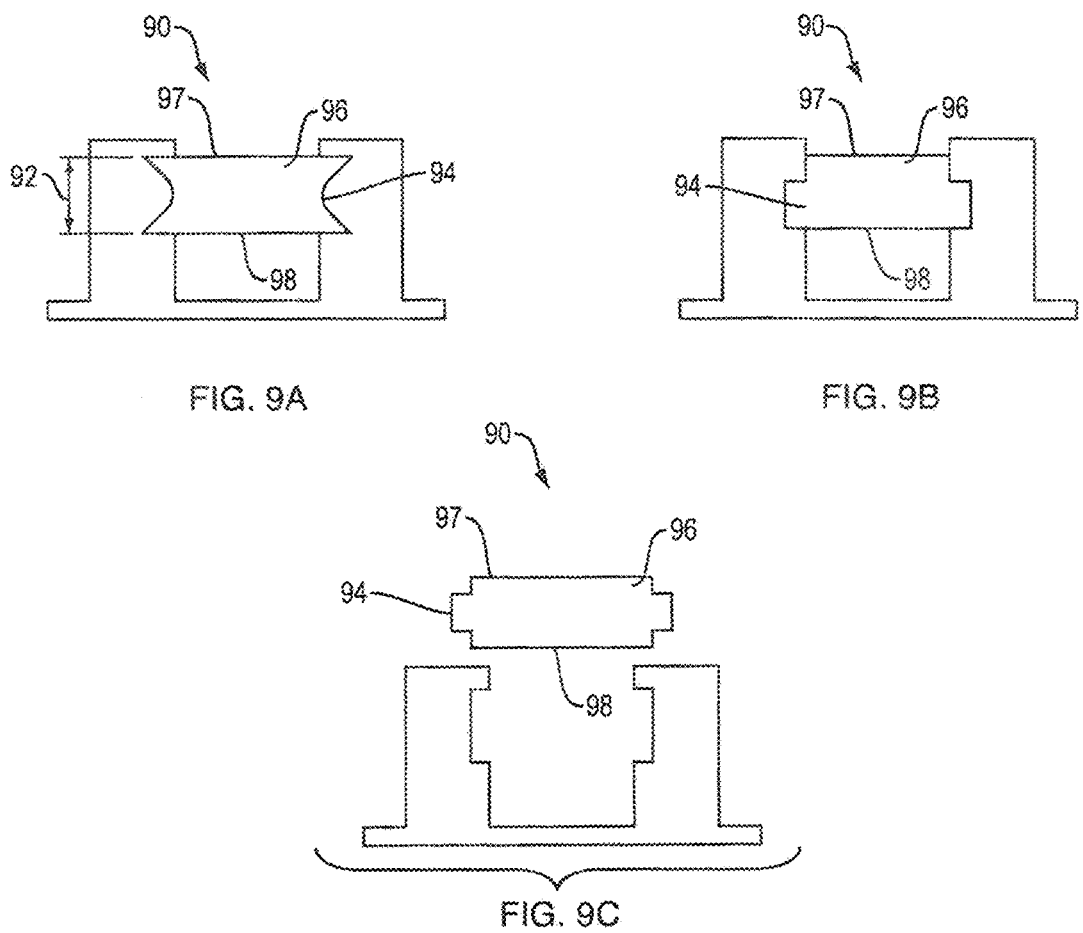
FIG. 9A  FIG. 9B
FIG. 9C

HIGH-FLOW PORT AND INFUSION NEEDLE SYSTEMS

CROSS-REFERENCE TO RELATED APPLICATIONS

This application is a continuation-in-part of U.S. Non-Provisional application Ser. No. 14/593,502, filed on Jan. 9, 2015, which claims the benefit of U.S. Provisional Application No. 61/925,287 filed on Jan. 9, 2014, both of which are incorporated herein by reference in its entireties.

FIELD OF THE INVENTION

The present invention relates generally to the field of vascular access ports. More specifically, the present invention relates to multi-reservoir port and infusion needle systems that support high-flow applications such as hemodialysis and apheresis.

BACKGROUND OF THE INVENTION

Multi-lumen catheters are commonly used for extracorporeal procedures in which blood is removed from the vascular system through an aspiration lumen, treated and returned to circulation through an infusion lumen. Apheresis is one example an extracorporeal procedure in which a patient's blood is removed from the vascular system, passed through a machine that removes specific blood components (e.g., plasma, red blood cells, white blood cells and/or platelets etc.) and then returned to circulation. Apheresis procedures generally last from one to four hours, although these times may vary depending on the procedure being performed, the medical condition being treated, the size of the patient and the type of machine being used. The number of treatments also varies based on the procedure being performed. Some procedures, such as red blood cell exchange, are only performed once. In other situations the patient is re-evaluated after two or three procedures to determine if they are responding to the treatment. Certain diseases require a pre-set treatment schedule that may include, for example, five procedures over the course of two weeks. Other procedures require the patient to follow a routine schedule of treatment that may vary from multiple times per week to once per month. Examples of apheresis procedures that require frequent treatments include plasma exchange (e.g., the removal of harmful substances from the blood plasma and subsequent replacement with saline, normal serum albumin or fresh frozen plasma); low density lipoprotein (LDL) apheresis (e.g., to treat familial hypercholesterolemia); photopheresis (e.g., to treat graft-versus-host disease; cutaneous T-cell lymphoma; or heart transplant rejection); allo- and autoantibody removal (e.g., to treat autoimmune disease; hemophilia; or transplant rejection); leukocytapheresis (e.g., to remove malignant white blood cells in leukemia) and thrombocytapheresis (e.g., to treat essential thrombocythemia; or polycythemia vera). Hemodialysis is another example of an extracorporeal procedure in which waste products, such as creatinine, urea, potassium, phosphate and/or free water, are removed from the blood of a patient whose kidneys are in a state of renal failure. In general, hemodialysis treatments are required once a patient has lost 85 to 90 percent of their kidney function. A typical treatment schedule requires performing hemodialysis 3 times a week, although patients who have retained substantial residual kidney function might only require sessions twice-a-week. Larger patients, or patients who have difficulties with fluid overload, may require four hemodialysis sessions per week are often prescribed for larger patients. Short daily home hemodialysis treatments may be performed as frequently as five to seven times per week. While both procedures require the continued re-circulation of blood through an external apparatus, the flow rates required for hemodialysis generally exceed those required for apheresis. For example, hemodialysis typically requires flow rates in the range 300-400 ml/min, but can sometimes exceed 800 ml/min. By contrast, the flow rates required for apheresis procedures can range from 30-60 ml/min (e.g., red blood cell exchange) to 150 ml/min (e.g., plasma exchange).

Medical professionals often prefer the use of implantable ports over peripherally inserted central catheters (i.e., PICCs) for procedures such as apheresis and hemodialysis that require repeated and/or prolonged access to the vascular system. One advantage of implantable ports is that they are completely indwelling, and therefore minimize the risk of infection, especially in patients requiring chronic care. Implantable ports are also more amenable to patients with active lifestyles since their relatively low profile allows them to be easily hidden from view. Ports are typically implanted in the patient's chest and connected to a catheter having a distal tip positioned at the point of treatment. For example, for many medical procedures the catheter tip is positioned at the junction of the superior vena cava and the right atrium. Implantable ports generally include a reservoir (i.e., chamber) in fluid communication with a catheter. The reservoir is typically covered by a needle-penetrable and self-sealing elastomeric septum. The self-sealing septum allows the reservoir to be accessed by puncturing both the patient's skin and the septum with a needle, for example, to infuse and/or aspirate fluid to and from the distal tip of the catheter.

For medical procedures that require multi-lumen access to the vascular system it is common for two ports to be implanted within the patient. While a variety of arrangements are possible, it is most common for one port to be implanted within the patient's left arm and the other port implanted within the right arm. In addition to the increased cost associated with implanting two ports, the separate invasive procedures dramatically increase patient discomfort and the likelihood of negative outcomes such as infection. These problems may be avoided by implanting a multi-reservoir port, which allows the administration of fluid through one reservoir and aspiration of fluid through a separate reservoir. While multi-reservoir ports are more cost-efficient, minimize patient discomfort and decrease patient exposure, they do have drawbacks.

Since fluid flows through a conventional multi-reservoir port (including the catheter) as a continuous stream, it is important that pressure on the aspiration side remains equal (i.e., balanced) to the pressure on the infusion side. With the power source for fluid flow provided by the apheresis or hemodialysis machine, fluid is essentially pulled through the aspiration side under negative pressure and pushed through the infusion side under positive pressure. This requires fluid on the aspiration side to travel a greater distance to reach the power source than fluid on the infusion side, resulting in the formation of high intraluminal negative pressures. These negative pressures force the lumen of the aspiration catheter to collapse or constrict, thereby restricting the flow of fluid throughout the entire system. To avoid harming the patient, automated apheresis and hemodialysis machines are designed to set-off pressure alarms when high intraluminal pressure is detected.

To maintain the proper pressure balance within multi-reservoir port systems, medical professionals typically access the aspiration reservoir of conventional multi-reservoir port systems with a 16 gauge needle. The large inner diameter of the 16 gauge needle is preferred over smaller 18 or 19 gauge needles because they allow fluid to flow into the aspiration reservoir under minimal pressure such that pressure alarms are not set-off. Due to its large inner diameter, a trocar is inserted into the lumen of the 16 gauge needle to prevent coring of the elastomeric septum covering the aspiration reservoir. Unfortunately, the size and shape of standard 16 gauge trocar needles creates large puncture sites within the elastomeric septum. Repeated overlapping punctures by the 16 gauge trocar eventually result in the formation of leakage sites within the septum, ultimately rendering the port unsuitable for safe and reliable use.

As evidenced by the competing interests of maintaining septum integrity and avoiding high intraluminal negative pressure, there is a continuing need for multi-reservoir port and non-coring needle systems that support high-flow applications with minimal impact on the puncture life of the elastomeric septum.

SUMMARY OF THE INVENTION

The present invention relates generally to multi-reservoir port, catheter and non-coring needle systems that support high-flow applications such as hemodialysis and apheresis. In one aspect, the present invention relates to improved port, catheter and needle systems that provide, both alone and in combination, optimal flow rates and septum puncture life with minimal intraluminal pressure.

In one embodiment, the present invention relates to a high flow multi-reservoir port assembly, comprising a vascular access port that includes a housing defining first (i.e., aspiration) and second (i.e., infusion) reservoirs. A first septum is mounted within the housing to seal the first reservoir, and a second septum is mounted within the housing to seal the second reservoir. The first and second septa (plural) are configured to be penetrable by a needle, and self-sealing after the needle is withdrawn. An inlet stem with an inlet lumen is in fluid communication with the first reservoir, and an outlet stem with an outlet lumen is in fluid communication with the second reservoir. The inlet and outlet stems are in fluid communication with a dual-lumen catheter that includes a proximal end, a distal end and first and second lumens extending therebetween. The catheter includes a smooth outer surface having a substantially circular outer diameter. The inlet stem is dimensioned to receive the first lumen at the proximal end of the catheter, and the outlet stem is dimensioned to receive the second lumen at the proximal end of the catheter. The first and second septa comprise an elastomeric material, including, for example, a multi-durometer material. The elastomeric material is self-sealing. The multi-durometer elastomeric material may comprise a first layer with a first durometer and a second layer with a second durometer. For example, the durometer of the material of the first layer may be less than the durometer of the material of the second layer. The first layer may be disposed above (i.e., on top of) the second layer. Alternatively, the first layer may surround the second layer. The first layer may also be disposed both above and below the second layer, such that the second layer is effectively sandwiched between two first layers. The first and second layers may include a variety of thicknesses. For example, the thickness of the second layer may be greater than the thickness of the first layer. Alternatively, the thickness of the first and second layers may be substantially the same. The first lumen of the catheter comprises a first inner diameter, and the second lumen of the catheter comprises a second inner diameter, wherein the second inner diameter is smaller than the first inner diameter. The first and second lumens of the catheter may include a variety of shapes. For example, the first inner diameter may define a substantially oval shape, while the second inner diameter may define a substantially concave shape. The first and second lumens of the catheter also define respective first and second openings at the distal end of the catheter. The openings do not necessarily terminate at the same location along the length of the catheter. For example, the first opening may be located proximal to the second opening. That is, the second opening may be located at or near the distal tip of the catheter, while the first opening is located at a position closer to the port. The first opening may also be substantially perpendicular to the second opening.

In another aspect, the present invention relates to a needle assembly, comprising at least one infusion needle and at least two aspiration needles. The at least one infusion needle is configured to penetrate the second septum of the second reservoir, while the at least two aspiration needles are configured to penetrate the first septum of the first reservoir (described above). The aspiration and infusion needles are, therefore, in fluid communication with the aspiration and infusion reservoirs, respectively. The at least one infusion needle and the at least two aspiration needles may include non-coring (i.e., Huber) needles. Needles of any size (i.e., gauge) may be used, for example, both the infusion and aspiration needles may be at least 19 gauge. To establish optimal fluid flow, the at least two aspiration needles may include openings that face in substantially opposite directions. Alternatively, the openings of the at least two aspiration needles may be configured such that they both face the inlet port of the aspiration reservoir. The at least two needles may be attached to each other, at for example, a y-site. The infusion needle may also include an opening configured to face the outlet port of the infusion reservoir. The at least two aspiration needles and at least one infusion needle allow the aspiration and infusion reservoirs to be in fluid communication with a blood circulation apparatus, such as an apheresis or hemodialysis machine.

In another embodiment, the present invention contemplates kits for the practice of the methods of this invention. The kits may include one or more containers containing a multi-reservoir implantable port, an aspiration needle assembly, an infusion needle assembly and catheter.

As used herein, "coring" refers to any portion of the septum that is forced into the shaft of a needle as the needle tip advances through the septum body. Septum coring produces small, detached particles that may become trapped in the cardiovascular system of the patient. In addition to potentially harming the patient, these particles can obstruct fluid flow through the needle assemblies and/or outlet stem of the multi-reservoir port. While a septum is capable of withstanding a certain number of coring events, continued coring creates a series of small passageways that extend through the body of the septum and eventually lead to various forms of septum failure. To at least partially address this problem, non-coring (e.g., Huber) needles are preferably used in conjunction with aspiration and infusion assemblies for accessing port reservoirs. Unlike traditional hypodermic needles, non-coring Huber needles pierce the septum in a knife-like fashion, thereby facilitating the resealing of the septum so that the aforementioned problems are largely averted.

As used herein, "trocar" refers to a surgical instrument having a sharpened point used to puncture a percutaneous surface for a variety of minimally invasive medical applications. In one embodiment, the body of the trocar includes a hollow tube through which a variety of medical instruments can be inserted into a patient's body. Alternatively, the body of the trocar can include a solid shaft, or sealed tube, dimensioned to fit within and reversibly occlude the lumen of a needle. The pointed tip of the trocar extends beyond, or is substantially flush with, the pointed end of the needle. Once the target surface (e.g., the skin, septum etc.) has been penetrated, the trocar is removed such that the lumen of the needle remains in fluid contact with the selected reservoir, chamber or body site.

As used herein, "durometer" refers to the measurement of a material's resistance to permanent indentation (i.e., hardness), and is typically used in reference to polymers, elastomers rubbers and the like. A material's durometer value can be determined by measuring the depth of an indentation in the material created by a given force on a standardized pressure foot. The depth of the indentation within the material is dependent on a variety of factors, including the density of the material, its viscoelastic properties, the shape of the pressure foot and the duration of the test.

As used herein, a "staggered tip" refers to a dual-lumen catheter that prevents fluid recirculation by positioning the entry site of the aspiration lumen away from the exit site of the infusion lumen (located at or near the catheter tip). Staggered-tip catheter designs are known in the art, including for example U.S. Pat. No. 8,317,773 and D603,044, herein incorporated by reference. The staggered tip design ensures that treated blood exiting the infusion lumen is carried away from the catheter tip as it re-enters circulation.

Other aspects, features, and advantages of the present invention are outlined in the detailed description, drawings, and claims.

BRIEF DESCRIPTION OF THE DRAWINGS

Non-limiting embodiments of the present disclosure will be described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure.

FIGS. 8A-C provide a schematic illustrations of various multi-durometer septum designs, in accordance with one embodiment of the present invention.

FIGS. 9A-C provide a schematic side view of septum and port geometries, in accordance with embodiments of the present invention.

DETAILED DESCRIPTION OF THE INVENTION

Figure 1A:
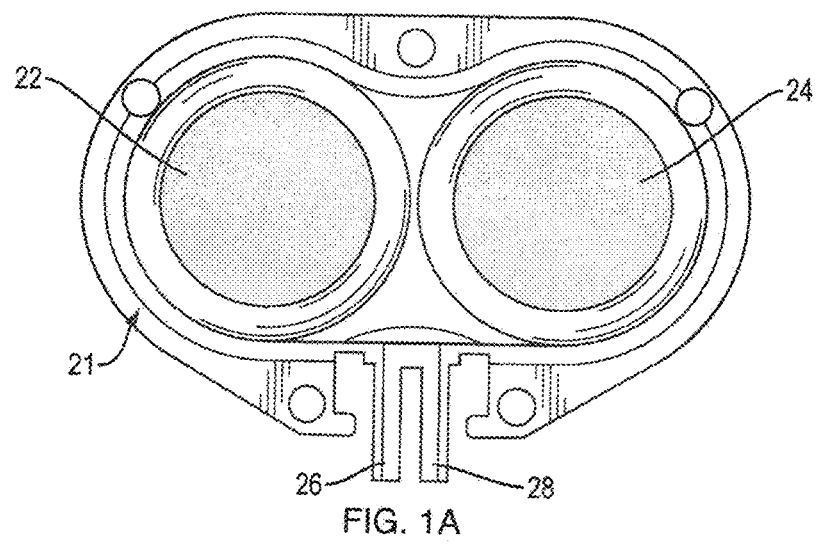
FIGS. 1A-C provide a top view of a multi-reservoir port system, in accordance with one embodiment of the present invention.

The present invention may be further understood with reference to the following description and the appended drawings, wherein like elements are referred to with the same reference numerals. The systems and methods of the present invention relate to multi-reservoir port, catheter and needle systems that support high-flow applications such as hemodialysis and apheresis. However, those skilled in the art will understand that the present invention is equally pertinent to a wide range of applications that benefit from the implantation of multi-reservoir ports with self-sealing septa, and which are accessible by a corresponding non-coring needle assembly.

As described herein, the present invention improves upon various components of conventional implantable port, needle-assembly and catheter designs to provide a system capable of maintaining balanced intraluminal fluid pressure required for high flow applications, without a corresponding decrease in septum puncture life. These advantages include 1) needle designs and configurations that provide optimal fluid flow and minimize damage to the septum, 2) dual-durometer septum designs and configurations that optimize self-sealing and minimize coring and 3) dual-lumen catheter designs and configurations that facilitate low pressure fluid flow within the aspiration lumen and prevent lumen constriction/collapsing. The cumulative effect that results from combining any, or all, of these improvements into a single system exceeds the improvements realized by an individually improvement alone. These improvements provide direct and immediate benefits to both the patient and medical professional. For example, the multi-reservoir ports decrease patient discomfort during implantation by requiring only a single invasive procedure, and are easier to conceal than separate single-reservoir ports implanted at different locations within the body. Patient discomfort is also decreased during treatment by limiting needle punctures through the skin to a single access site. Additionally, the ability to withstand a high number of needle punctures without septum failure allows expensive and invasive port replacement procedures to be postponed, or avoided altogether. This represents a significant savings in terms of medical costs, as well patient discomfort and risk exposure to.

Figure 1B:
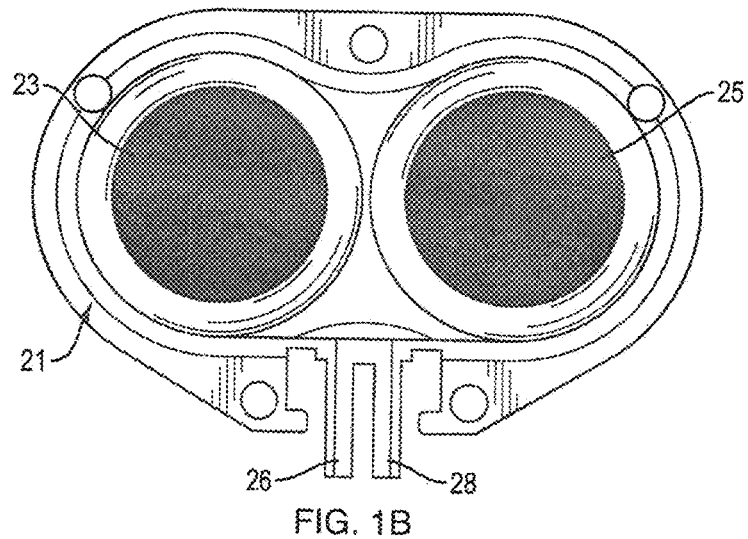
Figure 1C:
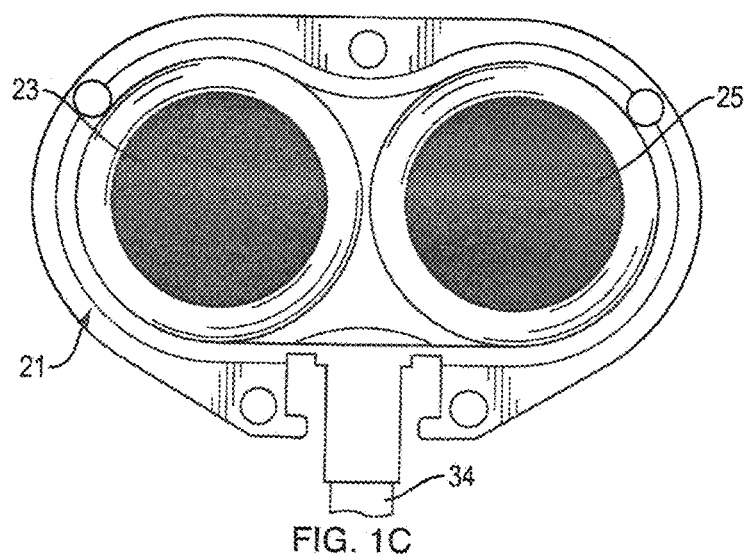

Multi-reservoir ports typically used in situations that require multi-lumen access to the vascular system. Examples of multi-reservoir ports, including the manner of fabrication and method of use are described in U.S. Patent Publication Nos. 20130150811 and 20090118683, each of which is assigned to AngioDynamics, Inc. of Latham, N.Y., and are fully incorporated herein by reference. Referring to FIG. 1, in one embodiment the present invention provides a multi-reservoir port 20 of the present invention includes a housing 21 that defines an aspiration reservoir 22 and an infusion reservoir 24 (i.e., first and second reservoirs, respectively). The aspiration 22 and infusion 24 reservoirs are covered and sealed by a first 23 and second 25 elastomeric septum, respectively. Each septum generally comprises a flexible membrane selected for its ability to continually re-seal the port reservoir following repeated punctures by a needle. An inlet stem 26 that defines an inlet lumen (not shown) is in fluid communication with the aspiration reservoir 22, and an outlet stem 28 that defines an outlet lumen (not shown) is in fluid communication with the infusion reservoir 24. The inlet 26 and outlet 28 stems are dimensioned to receive the proximal end 32 (i.e., proximal tip) of a dual-lumen catheter 30.

Figure 2A:
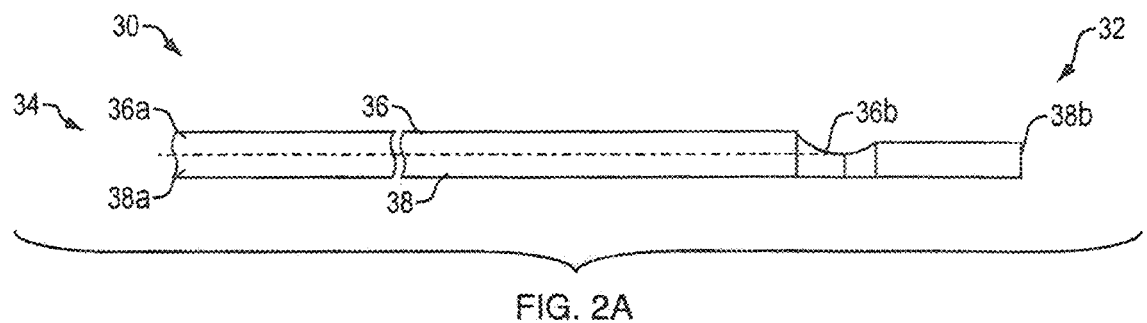
FIGS. 2A-B provides a schematic side-view of a staggered-tip catheter designs, in accordance with one embodiment of the present invention.
Figure 2B:
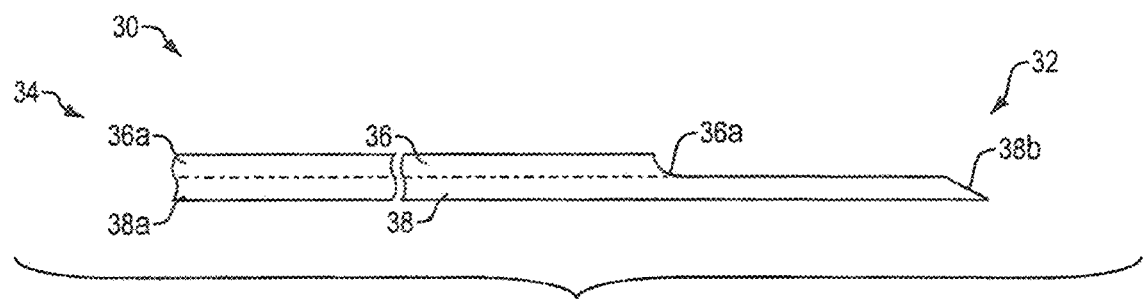

Referring to FIG. 2, in one embodiment the dual-lumen catheter includes a proximal end 32 and a distal end 34, with aspiration 36 and infusion 38 lumens (i.e., first and second lumens, respectively) extending therebetween. The aspiration lumen 36 at the distal end 34 of catheter 30 includes an opening 36a dimensioned to receive the inlet stem 26 of the multi-reservoir port 20 (FIG. 1C), such that the proximal end 32 of the catheter 30 is in fluid communication with the aspiration reservoir 22. Similarly, the infusion lumen 38 at the distal end 34 of catheter 30 includes an opening 38a dimensioned to receive the outlet stem 28 of the multi-reservoir port 20 (FIG. 1C), such that the proximal end 32 of the catheter 30 is in fluid communication with the infusion reservoir 24. The proximal end 32 of the dual-lumen catheter 30 includes a proximal opening 36b of the aspiration lumen 36 that is located distal to the proximal opening 38b of the infusion lumen 38. Additional examples of dual-lumen catheters are described in U.S. Pat. Nos. 7,410,602 and 8,317,773, each of which is assigned to Angiodynamics, Inc. of Latham, N.Y., and are fully incorporated herein by reference.

Figure 3:
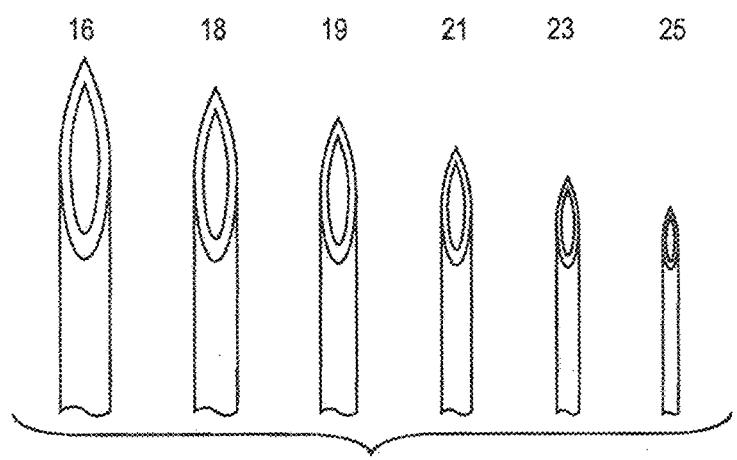
FIG. 3 provides a side-by-side comparison of the size of various gauge needles known in the art.

Medical procedures such as apheresis or hemodialysis require the septa covering the aspiration and infusion reservoirs to be frequently and repetitively punctured with a needle. The cumulative damage resulting from these needle penetrations gradually degrades the elastomeric septum until it is eventually unable to re-seal itself. The number of punctures that a septum can withstand depends on the size of the port, the type of elastomeric material, the durometer of the elastomeric material and the size of needle(s). FIG. 3 provides a side-by-side comparison of the relative sizes of standard needles used for various medical procedures. As would be expected, larger gauge needles cause more damage and decrease the "puncture life" or "stick life" of the septum. A typical septum is able to withstand approximately 50-100 punctures by a 16 gauge needle before its integrity is compromised to the point that it must be replaced. By contrast, the same septum can withstand upwards of 500 punctures by a standard 19 gauge needle. Thus, while a 16 gauge needle may provide the fluid dynamics required for high flow rate procedures, the inherent reduction in septum puncture life is not sustainable for frequently repeated procedures such as apheresis and hemodialysis.

Figure 4A:
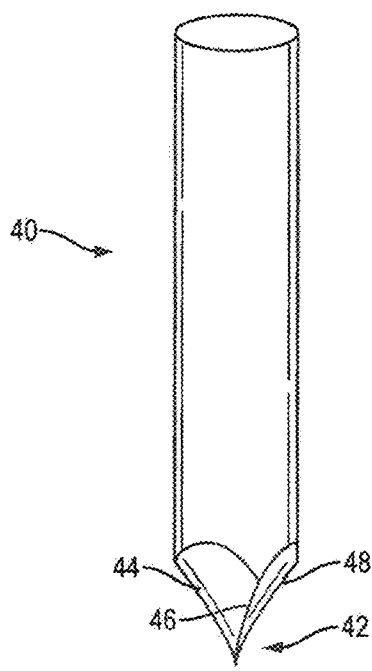
FIG. 4A provides a schematic view of a conventional 16 gauge trocar needle as recognized in the art.
Figure 4B:
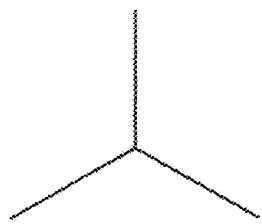
FIG. 4B provides a schematic top-view of a three-legged insertion profile using the trocar of FIG. 4A.
Figure 4C:
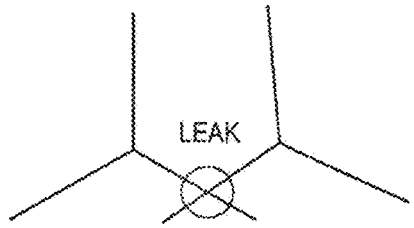
FIG. 4C provides a schematic top view of overlapping three-legged insertion profiles using the trocar of FIG. 4A.
Figure 4D:
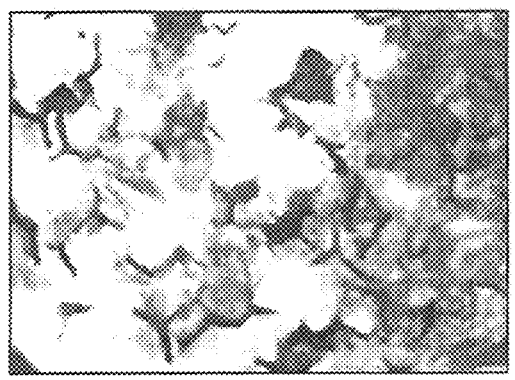
FIG. 4D depicts multiple and overlapping three-legged insertion sites through a septum using the trocar of FIG. 4A.
Figure 4E:
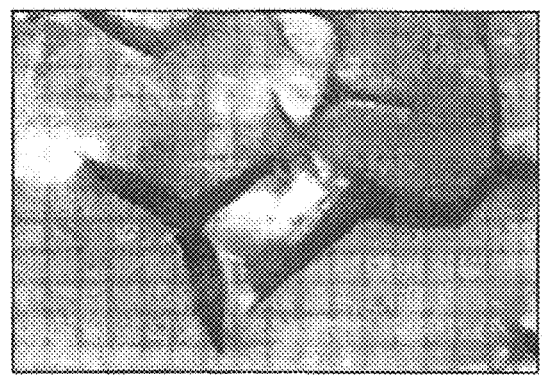
FIG. 4E depicts a magnified view of an overlapping three-legged insertion site of FIG. 4D.
Figure 5A:
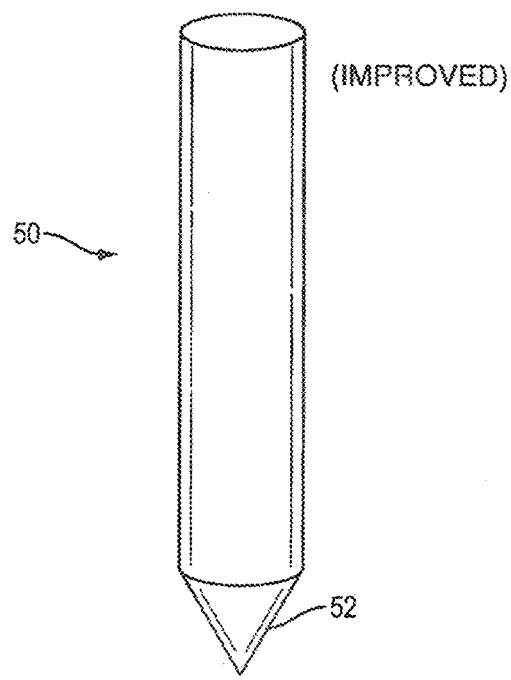
FIG. 5A provides a schematic view of a rounded singular point trocar, in accordance with one embodiment of the present invention.
Figure 5B:
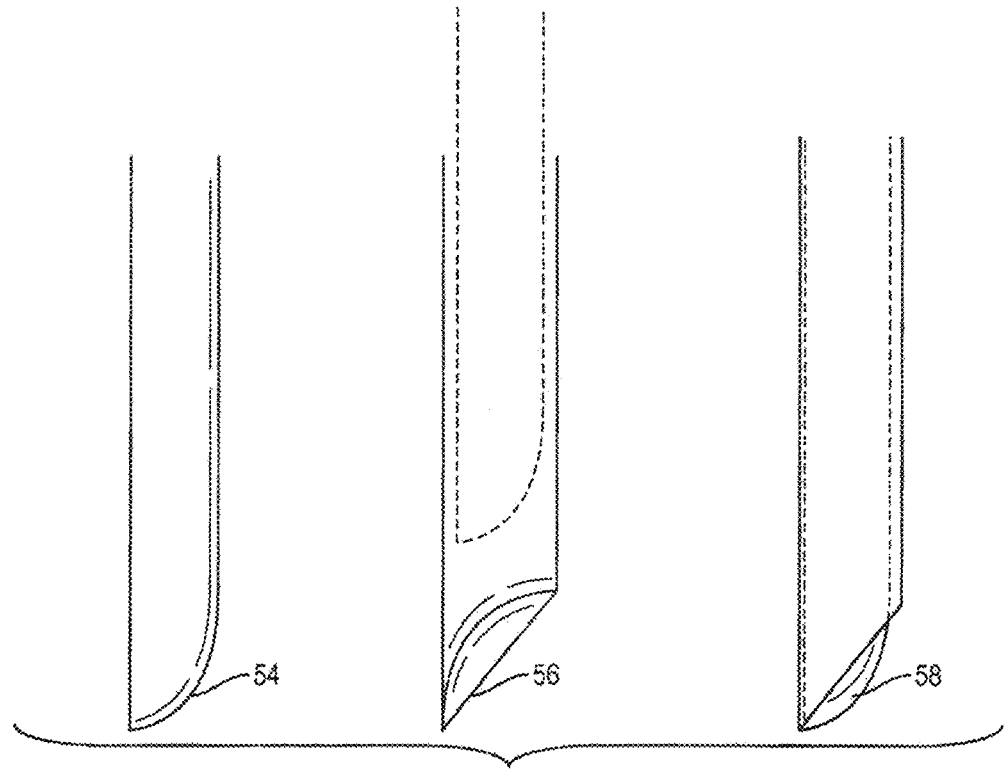
FIG. 5B provides a schematic side view a trocar that includes a unidirectional face, in accordance with one embodiment of the present invention.

FIG. 4A depicts a standard 16 gauge trocar needle 40 that includes a pointed tip 42 with three sharp edges 44, 46, 48 that create three-legged insertion profile (FIG. 4B) when advanced through the surface of an elastomeric septum. As shown in FIG. 4C, a gap is created when the legs of one or more adjacent puncture sites overlap, increasing the likelihood of the septum leaking from that location. As shown in FIG. 4D and FIG. 4E (magnified), repeated punctures of an elastomeric septum with the trocar such as the one depicted in FIG. 4A create multiple overlapping puncture sites that eventually compromise the integrity of the septum. Referring to FIG. 5A, in one embodiment an improved trocar needle 50 replaces the sharp edges of the conventional trocar tip with a singular rounded point 52. Replacing the sharp/rigid cutting edges with a smooth pointed surface increases the puncture life of the septum by providing a reduced insertion profile that decreases the likelihood of adjacent puncture sites overlapping. Referring to FIG. 5B, in another embodiment an improved trocar design includes a unidirectional face 54 configured to mirror the bevel of the needle opening 56. When inserted into the shaft of the needle, the unidirectional face 54 at the tip of the trocar conforms to the bevel of the needle opening 56 to create a solid unitary pointed tip 58. Unlike the rounded trocar of FIG. 5A, in which the septum is punctured entirely by the trocar tip, the pointed tip depicted in FIG. 5B represents the combined points of the needle opening and trocar.

Figure 6A:
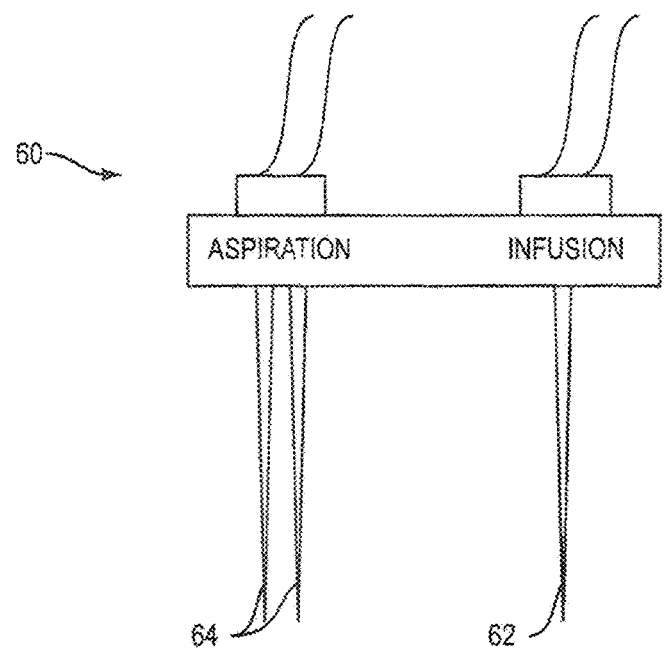
FIG. 6A provides a schematic side view a needle aspiration and infusion system, in accordance with one embodiment of the present invention.

Referring to FIG. 6A, in one embodiment an infusion needle assembly 60 comprising two non-coring 19 gauge needles 64 for penetrating the septum of the aspiration reservoir 22 (not shown) and a single 19 or 20 gauge needle 62 for penetrating the septum of the infusion reservoir 24 (not shown). In one embodiment, the two non-coring 19 gauge needles are connected to each other by tubing that bifurcates to form a y-site such that a medical professional can simultaneously puncture the septum of the aspiration reservoir with both needles. The embodiment depicted in FIG. 6A is not intended to limit the arrangement, orientation, gauge or number of needles used to penetrate the septum of the aspiration or infusion reservoirs. Table 1 provides a comparison of the inner diameter (ID) of various needle sizes, along with the corresponding number of needles of each gauge required to meet the internal cross-sectional area of a 16 gauge needle. Any number and/or combination of needles in Table 1 can be used to access the aspiration and/or infusion lumens described herein, depending on the desired flow rate, clinical application and condition of the patient.

TABLE 1

| Needle Size | ID (in) | Area (in^2) | # of needles to equal 16 G Area |
| --- | --- | --- | --- |
| 16 G | 0.047 | 0.00694 | 1 |
| 17 G | 0.042 | 0.00554 | 1.25 |
| 18 G | 0.033 | 0.00342 | 2.03 |
| 19 G | 0.027 | 0.00229 | 3.03 |
| 20 G | 0.02375 | 0.00177 | 3.92 |
| 22 G | 0.01625 | 0.00083 | 8.37 |

Although two non-coring 19 gauge needles provide less cross-sectional area than a single 16 gauge needle, the fluid pressure they achieve is sufficiently similar to that of 16 gauge needle to prevent the aspiration lumen from constricting and/or collapsing upon itself. The ability of two 19 gauge needles to achieve fluid pressures that maintain aspiration lumen integrity similar to one 16 gauge needle while providing a higher clinically acceptable number of septum punctures represents a significant clinical advantage for high flow procedures.

Figure 6B:
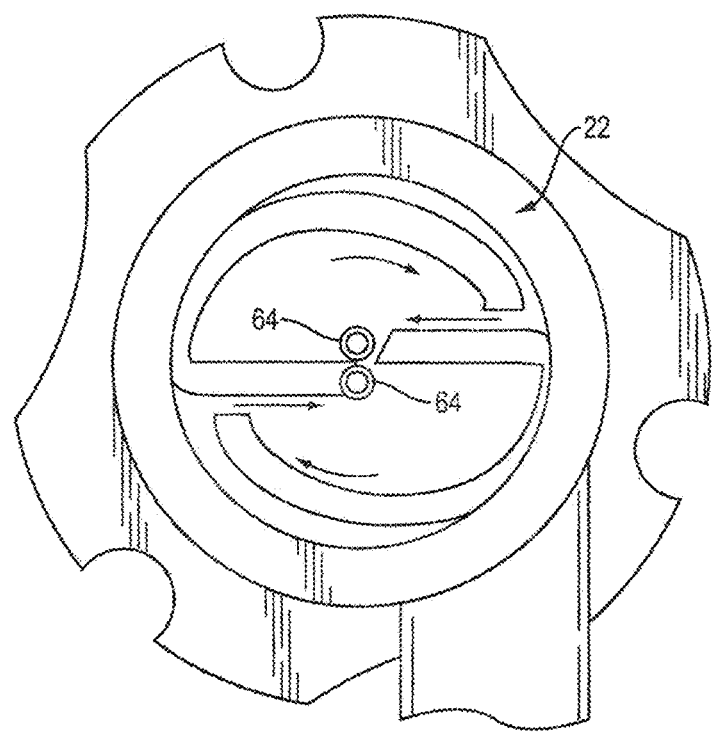
FIG. 6B provides a top view of an aspiration reservoir with vortex fluid flow, in accordance with one embodiment of the present invention.

In one embodiment, fluid flow may be further optimized by adjusting the orientation of each needle opening (i.e., bevel) in the needle assembly depicted in FIG. 6A. Since the position of the multi-reservoir port is visible underneath the skin, the openings of the linked non-coring needles may be positioned such that they face directly towards the inlet lumen. Alternatively, as shown in FIG. 6B, in another embodiment the openings of the linked non-coring needles 64 (top view) are positioned such that they face in substantially opposite directions to facilitate vortex (i.e., spiral) flow within the aspiration reservoir. As described in U.S. Pat. No. 5,951,512 assigned to Angiodynamics, Inc. of Latham, N.Y., incorporated herein by reference, vortex flow within a port reservoir provides a number of benefits, including the prevention of unwanted buildup of blood components within the port reservoirs. As indicated by the direction of the arrows, facing the aspiration needles 64 such that their respective openings face opposite directions encourages the fluid to flow in a vortex pattern within the aspiration reservoir. The pattern of flow depicted in FIG. 6B allows fluid to flow into each needle opening from opposite, and therefore non-competing, portions of the circulating vortex. It should be appreciated that vortex flow can be established in both the aspiration reservoir (i.e., as fluid is drawn into the needle openings) and infusion reservoir (i.e., as fluid flows out of the needle openings) by adjusting the orientation of the needle opening(s) within the aspiration or infusion reservoir.

Figure 7A:
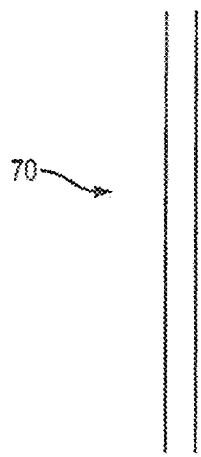
FIGS. 7A-C provide schematic side views of needle shaft designs, in accordance with embodiments of the present invention.
Figure 7B:
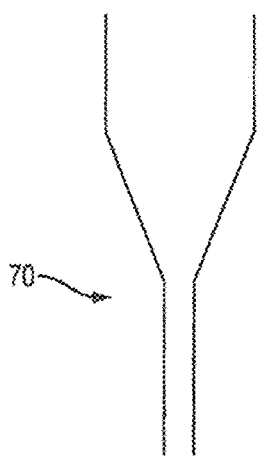
Figure 7C:
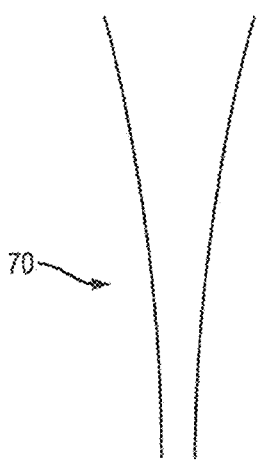

In yet another embodiment, flow rates through the aspiration and/or infusion needle assemblies can be further optimized by using needle shaft designs that reduce the pressure required to meet the desired flow rates. For example, the length of the small inner diameter of a needle of standard length and shape (FIG. 7A) can be minimized by providing a needle shaft that flares (FIG. 7B) or gradually tapers (FIG. 7C) to a wider inner diameter at a point above the needle tip, thereby reducing the pressure drop over the length of the needle. The wider portions of the needle shaft of FIGS. 7B and 7C are sufficiently distant from the pointed tip of the needle to cause minimal trauma to both the patient and port septum.

Since ports are fully implanted within the body, their service life is limited in large part by the durability (i.e., puncture life) of the septum. Septum puncture life, and therefore the life of the multi-reservoir port, can be optimized by careful selection of the septum material and the dimensions of the septum within the port assembly. Examples of needle-penetrable and self-sealable materials include, but are not limited to, silicone and related elastomeric materials. Regardless of the material used, after a threshold number of needle punctures the septum becomes damaged and is no longer able to re-seal itself. Once the integrity of the septum is compromised to the point that it can no longer prevent fluid leakage, either into or out of the port reservoir, it is necessary to replace the entire port assembly, and possibly the attached catheter as well. Generally, the ability of a septum to self-seal and resist coring is directly related to the durometer of the material it is constructed from. While low durometer materials tend to reduce coring, they are not as effective at self-sealing after withdrawal of the needle. Similarly, high durometer materials promote better self-sealing after needle withdrawal, but tend to core relatively easily. Due to these competing requirements, the septum of conventional implantable ports generally include elastomeric materials having a durometer that resists coring and is capable of self-sealing, but is not optimal for either criteria.

In another embodiment, the present invention provides a septum comprising a dual-durometer elastomeric material that includes one layer configured to minimize coring (i.e., a low durometer material) and a second layer configured for optimal self-sealing (i.e., a high durometer material). Optimizing the self-sealing and non-coring capabilities of the septum with a dual-durometer materials enhances flow rates throughout the system by allowing repeated penetration with large gauge needles. For example, as shown in FIG. 8A, a dual-durometer septum 80 can be formed during the molding process to preferably include a top layer 82 (i.e., the layer closest to the patient's skin) comprising a low durometer material to reduce coring, and a bottom layer 84 (i.e., the layer closest to the port reservoir) comprising a high durometer material to promote self-sealing. While the top and bottom layers of FIG. 8A are depicted as being of substantially the same thickness, it should be understood that the thickness and orientation of either layer may be adjusted according to the clinical application and needs of the patient. For example, as shown in FIG. 8B, a thin layer of a low durometer material 82 may enclose (i.e., surround, encapsulate, encase etc.) a proportionally thicker layer of a high durometer material 84. Alternatively, as shown in FIG. 8C, the layer of high durometer material 84 may be disposed between top and bottom layers of low durometer material 82.

Figures 12A, 12B, 12C:
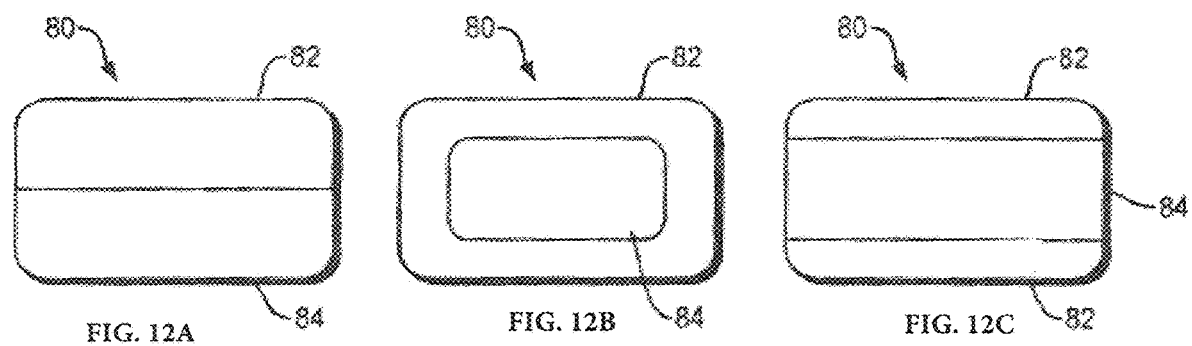
FIGS. 12A-12C provide schematic illustrations of various septum designs, in accordance with one embodiment of the present invention.

In an alternative embodiment of FIGS. 8A-8C, as shown in FIGS. 12A-12C, the septum 80 can comprise an outer layer 82 and an inner layer 84, wherein the outer layer 82 comprises a silicone layer and the inner layer 84 comprises a Non-Newtonian material. Newtonian materials are materials in which there is a linear relationship between shear stress and shear rate. The viscosity of Newtonian materials is dependent only on temperature. Non-Newtonian materials do not have a linear relationship between shear stress and shear rate and accordingly, the viscosity of the materials is dependent on the shear stress and shear rate. This allows Non-Newtonian materials to have different reactions to shear force when inserting something into the material, including making the material more viscous or less viscous. A Non-Newtonian material can be created by a colloidal suspension of small particles within a viscous fluid. The particles cause a "log jam" effect to occur when shear force is applied even at minimal thickness, as the effect can be on a nano scale. Embodiments of this design could range from a large center reservoir of the Non-Newtonian material down to multiple micro layers sandwiched between silicone or coated on the surface. Additionally, the Non-Newtonian material could be applied to fibrous materials like Kevlar and layered within the septum 80. The Non-Newtonian material used would be a combination of a liquid particle component and a solid particle component. Examples of the liquid particle component can be one of, but not limited to: liquid silicone, polyethylene glycol, polyborodimethylsiloxane, or glycerine. Examples of the solid particle component can be one of, but not limited to: silica particles, nano-silica particles mica particles, quartz particles, or plastic particles.

One of the benefits of using a Non-Newtonian material as the inner layer 84 of the septum 80 is that Non-Newtonian materials re-seal marks or holes from puncturing the inner layer 84 much more efficiently, as the inner layer can be less viscous, which can fill the holes or puncture marks left from accessing the septum 80. When the septum 80 is at rest, the inner layer 84 will be in a less viscous state. When shear is applied—in this case, when a needle is inserted into the inner layer 84—the inner layer 84 will transition from a less viscous state to a more viscous state to aid in the stability of the septum and the needle when delivering fluid through the needle. The increased stability of the septum and the needle is very helpful when power injecting through the multi-reservoir port 20. Once the needle is removed, the inner layer 84 will return back to its less viscous state and any hole or puncture mark left from inserting the needle will be filled from the flowing of the inner layer 84. Since the inner layer 84 will quickly fill any of the marks or holes left from inserting the needle, any remaining and/or permanent holes or marks will be limited to the outer layer 82 of the septum 80.

Alternatively, the Non-Newtonian material comprising the inner layer 84 of the septum 80 could be a more viscous material at rest. When shear is applied—in this case, when a needle is inserted into the inner layer 84—the inner layer 84 can transition from a more viscous state to a less viscous state only at the site where the needle creates shear to the Non-Newtonian material comprising the inner layer 84. This allows the Non-Newtonian material comprising the inner layer to seal any hole or mark left from the needle, while allowing the portion of the inner layer 84 not at the site where the needle creates shear in the inner layer 84 to remain more viscous.

Another benefit of using a Non-Newtonian material for the inner layer 84 of the septum 80 is that there is a seamless fit between the outer layer 82 and inner layer 84. When a septum is made with two layers of different durometers, the material with the lower durometer may not be able to completely seal the material with the higher durometer when the septum is accessed and fluid is delivered, causing leaks in the septum. Using a Non-Newtonian material for the inner layer 84 will reduce leaks because the Non-Newtonian material is in a less viscous state when at rest, which results in the inner layer 84 completely filling the empty space that is created when the outer layer 82 is created.

A method of manufacturing a septum 80 with an inner layer 84 of Non-Newtonian Material and an outer layer 82 of a Newtonian material is explained herein. The septum 80 could be formed in an encapsulated design, which can be manufactured in multiple ways. An outer layer 82 of silicone can be formed and a Non-Newtonian material can be injected into the outer layer 82 with a syringe or needle, creating the inner layer 84. Another way to form the septum 80 with an encapsulated design is to mold the Non-Newtonian material and then overmold the Non-Newtonian material with silicone. Another way that the septum 80 could be formed is by applying the Non-Newtonian material between layers of silicone. The Non-Newtonian material can be applied to the silicone in numerous ways, including being brushed onto each layer of the silicone using a brush or other applicator. Additionally, the Non-Newtonian material could be thinned with Ethanol and applied to a piece of material that will be placed in between the layers of silicone or can be overmolded in silicone, similar to the encapsulated design explained above.

Additionally, a method of manufacturing a septum 80 shown in FIG. 12C with an inner layer 84 of Non-Newtonian material and an outer layer 82 of a Newtonian material is explained herein. A first piece of the outer layer 82 made of a Newtonian material can be pressure fit into the bottom of the reservoir of the multi-reservoir port 20. Next, the inner layer 84 made of a Non-Newtonian material can be inserted on top of the first piece of the outer layer 82. Finally, a second piece of the outer layer 82 can be pressure fit on top of the inner layer 84. As the first piece and second piece of the outer layer 82 are pressure fit into the multi-reservoir port 20, the walls of the multi-reservoir port 20 aid in keeping the septum 80 stable and making sure the inner layer 84 does not leak.

In another embodiment, the dual-durometer characteristics of the multi-layer septum of FIGS. 9A-C may be achieved by applying varying degrees of radially inward compressive force along the height 92 of a single-layer septum to create high and low durometer regions throughout the length of the septum. Inward compression increases the ability of the septum to re-seal puncture sites by pushing the edges of puncture holes together. Portions of the septum that receive little, or no, inward compression provide improved self-sealing due to their decreased susceptibility to coring. In one embodiment, the radially compressive inward force is created by placing a septum having a constant cylindrical shape within a port housing that includes a varying inner diameter. For example, the port housing of FIG. 9A includes an inner wall 94 configured to exert a radially compressive inward force to the middle portion of the septum 96, and incrementally less compression along the top 97 and bottom 98 portions of the septum. Similar to the dual-durometer septum of FIG. 8C, the septum configuration of FIG. 9A provides a high durometer middle layer 96 disposed between low durometer top 97 and bottom 98 layers. The durometer gradient created by the port housing of FIG. 9A ensures that the self-sealing inner portion of the septum is surrounded by top and bottom layers that are increasingly resistant to coring (i.e., top and bottom surfaces). FIG. 9B illustrates another embodiment, in which a radially compressive inward force is applied primarily to the top 97 of the septum to provide a high durometer top layer and a low durometer bottom layer 98. In another embodiment, the radially compressive inward force results from placing a septum with a varying outer diameter (OD) within a port housing. For example, the septum of FIG. 9C includes a middle portion 96 that is wider than the top 97 and bottom 98 portions such that the port housing primarily compresses the middle portion 96 of the septum. Similar to the dual-durometer septum of FIG. 8C, the septum of FIG. 9C provides a high durometer middle layer 96 disposed between low durometer top 97 and bottom layers 98. The septum geometries and port housing geometries described herein are provided by way of non-limiting example. It should be appreciated that the present invention contemplates a variety of septum and port geometries beyond those disclosed herein.

Figure 10A:
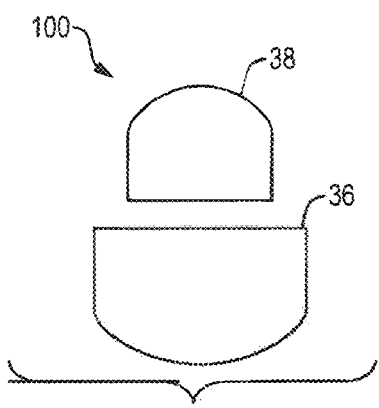
FIGS. 10A-D provide schematic illustration of various dual-lumen catheter designs, in accordance with one embodiment of the present invention.
Figure 10B:
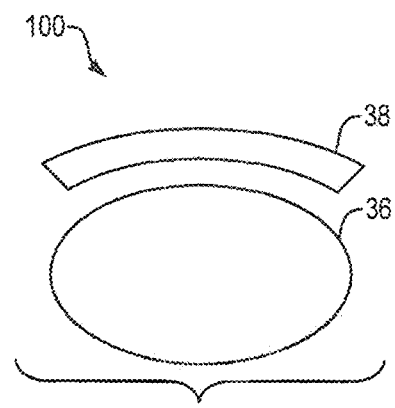
Figure 10C:
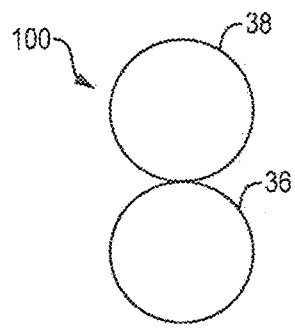
Figure 10D:
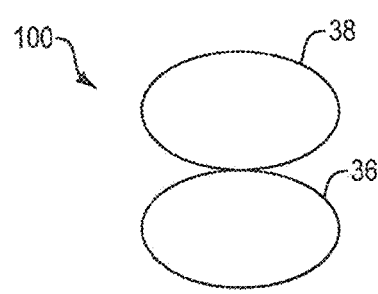
Figure 11:
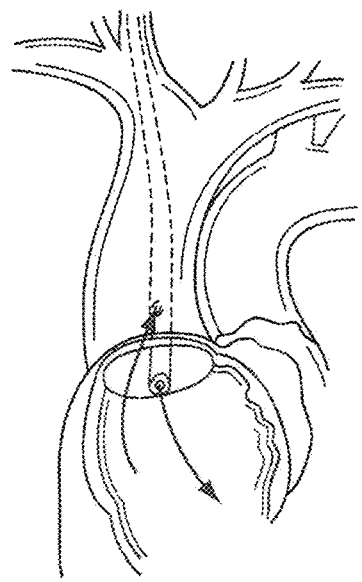
FIG. 11 depicts the placement of a staggered-tip dual-lumen catheter within a patient, in accordance with one embodiment of the present invention.

In one embodiment, flow rates may be further optimized by providing a dual-lumen catheter that includes an aspiration lumen that is over-sized as compared to the infusion lumen. The larger diameter of the aspiration lumen ensures that fluid flows from the proximal end of the catheter to the aspiration reservoir under minimal pressure. An additional benefit of using a dual-lumen that includes differently shaped aspiration and infusion lumens is that it becomes practically impossible to connect the distal end of the catheter to the incorrect inlet or outlet stem. As illustrated in FIG. 10A, the aspiration 36 and infusion 38 lumens may both include D-shapes, with the aspiration lumen having a larger internal diameter than the infusion lumen. Alternatively, as illustrated in FIG. 10B, the dual-lumen catheter may include a substantially oblong aspiration lumen 36 and a concave infusion lumen 38. An over-sized aspiration lumen is particularly useful for hemodialysis procedures, which require flow rates of at least 400 ml/min. However, the over-sized aspiration lumens required for hemodialysis may be unnecessarily larger for the comparatively low 150 ml/min flow rates required for apheresis. Referring to FIGS. 10C and 10D, dual-lumen catheters may be designed specifically for apheresis that include aspiration 36 and infusion 38 lumens that are both substantially circular (i.e., round, oval, oblong, elliptical etc.). Circular shaped lumens remain capable of proving the flow rates required for apheresis and provide better structural support than D-shaped designs to prevent the aspiration lumen from collapsing under negative pressure. As discussed above, the integrity of the infusion lumen is not an issue because fluid flows though the infusion lumen under positive pressure. However, a dual-lumen catheter in which both lumens are substantially circular is still beneficial because medical professionals commonly reverse the aspiration and infusion lumens during treatment. For example, if the aspiration lumen has a fibrin sheath buildup or other blockage reversing the direction of flow such allows blockages to be flushed away (i.e., into circulation). Thus, it remains important to have an infusion lumen capable of withstanding the negative pressures associated with an aspiration lumen.

All of the systems, assemblies and/or methods disclosed and claimed herein can be made and executed without undue experimentation in light of the present disclosure. While the present invention have been described in terms of preferred embodiments, it will be apparent to those of skill in the art that variations can be applied to the systems, assemblies and/or methods described herein without departing from the concept, spirit and scope of the invention. All such similar substitutes and modifications apparent to those skilled in the art are deemed to be within the spirit, scope and concept of the invention as defined by the appended claims.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. A vascular access port, comprising:
   a vascular access port housing comprising at least one reservoir;
   at least one septum situated within the at least one reservoir, the at least one septum comprising a septum first layer comprising a Newtonian material and a septum second layer comprising a Non-Newtonian material, the septum second layer being encapsulated by the septum first layer;
   at least one outlet stem having an outlet lumen, the at least one outlet stem in fluid communication with the at least one reservoir.

2. The vascular access port of claim 1, wherein the Newtonian material of the septum first layer comprises silicone.

3. The vascular access port of claim 1, wherein the Non-Newtonian material of the septum second layer is comprised of a combination of at least one liquid particle component and at least one solid particle component.

4. The vascular access port of claim 3, wherein the at least one liquid particle component comprises silicone, polyethylene glycol, or glycerine.

5. The vascular access port of claim 3, wherein the at least one solid particle component comprises silica, mica, or plastic particles.

6. A vascular access port, comprising:
   a housing comprising at least one septum;
   the at least one septum comprising a septum first layer comprising a Newtonian material and a septum second layer comprising a Non-Newtonian material, the septum second layer being encapsulated by the septum first layer.

7. The vascular access port of claim 6, wherein the Newtonian material of the septum first layer comprises silicone.

8. The vascular access port of claim 6, wherein the Non-Newtonian material is comprised of a combination of at least one liquid particle component and at least one solid particle component.

9. The vascular access port of claim 8, wherein the at least one liquid particle component comprises silicone, polyethylene glycol, or glycerine.

10. The vascular access port of claim 8, wherein the at least one solid particle component comprises silica, mica, or plastic particles.

11. A vascular access port, comprising:
    at least one septum, the at least one septum comprising a septum first layer comprising a Newtonian material, a septum second layer comprising a Non-Newtonian material, wherein the septum second layer is encapsulated by the septum first layer.

12. The vascular access port of claim 11, wherein the Newtonian material of the septum first layer comprises silicone.

13. The vascular access port of claim 11, wherein the vascular access port comprises a housing.

14. The vascular access port of claim 13, wherein the housing comprises a reservoir.

15. The vascular access port of claim 11, further comprising a housing comprising a reservoir and at least one outlet stem having an outlet lumen, the at least one outlet stem in fluid communication with the reservoir.

16. The vascular access port of claim 11, wherein the Non-Newtonian material is comprised of a combination of at least one liquid particle component and at least one solid particle component.

17. The vascular access port of claim 16, wherein the at least one liquid particle component comprises silicone, polyethylene glycol, or glycerine.

18. The vascular access port of claim 16, wherein the at least one solid particle component comprises silica, mica, or plastic particles.

* * * * *